United States Patent [19] [11] 4,046,805
Bernstein et al. [45] Sept. 6, 1977

[54] SUBSTITUTED-HYDROXY-NAPHTHALENEDISULFONIC ACID COMPOUNDS

[75] Inventors: Seymour Bernstein, New City, N.Y.; Robert Herman Lenhard, Paramus, N.J.; Milton David Heller, New City, N.Y.

[73] Assignee: American Cyanamid Company, Stamford, Conn.

[21] Appl. No.: 684,598

[22] Filed: May 10, 1976

[51] Int. Cl.$^2$ .................. C07C 143/30; A61K 31/185
[52] U.S. Cl. .............................. 260/506; 260/507 R; 424/315
[58] Field of Search ........................... 260/506, 507 R

[56] References Cited

U.S. PATENT DOCUMENTS

| 1,218,654 | 3/1917  | Heymann et al. | 260/506 |
| 1,308,071 | 7/1919  | Heymann et al. | 260/506 |
| 1,606,624 | 11/1926 | Fourneau       | 260/506 |
| 1,968,820 | 8/1934  | Dyson et al.   | 260/506 |

OTHER PUBLICATIONS

Spinks, Biochem. Journal, 42, 109 (1948).
Baker et al., J. Med. Chem., 12, 902 (1969).
Baker et al., J. Med. Chem., 12, 415 (1969).

*Primary Examiner*—James O. Thomas, Jr.
*Assistant Examiner*—Nicky Chan
*Attorney, Agent, or Firm*—Jack W. Richards

[57] ABSTRACT

Substituted-hydroxy-naphthalenedisulfonic acids, acid ureides and salts thereof useful as complement inhibitors.

4 Claims, No Drawings

SUBSTITUTED-HYDROXY-NAPHTHALENEDISULFONIC ACID COMPOUNDS

CROSS-REFERENCE TO RELATED APPLICATION

This application is related to concurrently filed and copending application Ser. No. 684,695, now U.S. Pat. No. 4,018,764.

BACKGROUND OF THE INVENTION

The present invention resides in the concept of certain (substituted)hydroxy-naphthalenedisulfonic acids, acid ureides and salts thereof, particularly new (substituted) 4-hydroxy-2,7-naphthalenedisulfonic acids and known (substituted) 4-hydroxy-2,7-naphthalenedisulfonic acids and 4-hydroxy-2,7-naphthalenedisulfonic acid ureides, all of which are useful as inhibitors of the complement system of warm-blooded animals.

The term "complement" refers to a complex group of proteins in body fluids that, working together with antibodies or other factors, play an important role as mediators of immune allergic, immunochemical and/or immunopathological reactions. The reactions in which complement participates takes place in blood serum or in other body fluids, and hence are considered to be humoral reactions.

With regard to human blood, there are at present more than 11 proteins in the complement system. There complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935–938 (1968); *Scientific American*, 229, (No. 5), 54–66 (1973); *Medical World News*, Oct. 11, 1974, pp. 53–58, 64–66; *Harvey Lectures*, 66, 75–104 (1972); *The New England Journal of Medicine*, 287, 489–495; 545–549; 592–596; 642–646 (1972); *The Johns Hopkins Med. J.*, 128, 57–74 (1971); and *Federation Proceedings*, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8, and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesion and skin eruptions. The treatment of diphtheria or tetanus with the injection of large amounts of antitoxin sometimes results in serum sickness, an immune-complex diseases. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, *British Journal of Experimental Pathology*, 33, 327–339 (1952). The compound 8,8'-[ureylene[m-phenylenecarbonylimino(4-methyl-m-phenylene)carbonylimino]]di-1,3,5-naphthalenetrisulfonic acid, hexasodium salt (Suramin Sodium) as a competitive inhibitor of the complement system, *Clin. Exp. Immunol.*, 10, 127–138 (1972). German Patent No. 2,254,893 or South African Pat. No. 727,923 discloses certain 1-(diphenylmethyl)-4-(3-phenylallyl)piperazines useful as complement inhibitors. U.S. Pat. No. 3,897,434 discloses certain pyrazolo[1,5c]-quinazolin-5(6H)-ones useful as complement inhibitors. The compound m-[m-(p-nitrophenylureido)phenozypropoxyl]benzamidine is also known as a complement inhibitor, *Immunology*, 26, 819 (1974). Other chemical compounds having complement inhibiting activity are disclosed in, for example, *Journal of Medicinal Chemistry*, 12, 415–419; 902–905; 1049–1052; 1053–1056 (1969); *Canadian Journal of Biochemistry*, 47, 547–552 (1969); *The Journal of Immunology*, 93, 629–640 (1964); *The Journal of Immunology*, 104, 279–288 (1970); *The Journal of Immunology*, 106, 241–245 (1971); and *The Journal of Immunology*, 111, 1061–1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812 (1972); *Allergol, Et. Immunopath*, II, 163–168 (1974); and *J. Allergy Clin. Immunol.*, 53, No. 5, 298–302 (1974).

SUMMARY OF THE INVENTION

Broadly, this invention is concerned with the use of substituted-hydroxy-naphthalenedisulfonic acids, acid ureides and salts thereof which can be represented by general formula (I):

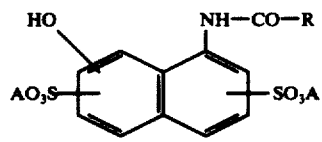
(I)

wherein R is selected from the group comprising

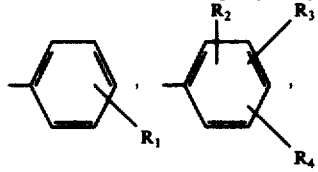

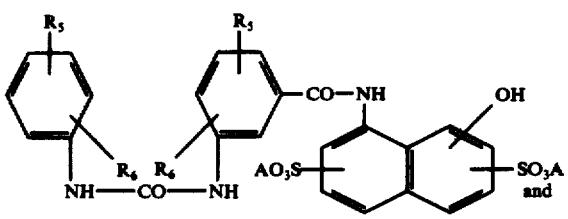
and

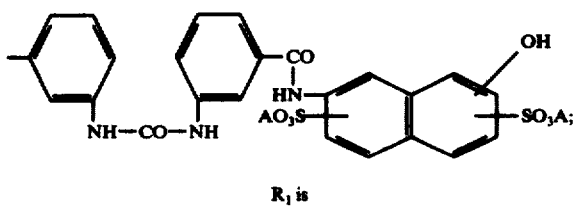

$R_1$ is

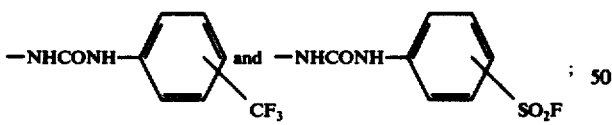

$R_2$ is hydrogen and —$CH_3$; $R_3$ is hydrogen, —$NO_2$, —$NH_2$ and —$CH_3$;
$R_4$ is hydrogen, —$NO_2$, —$NH_2$, —$CH_3$ and

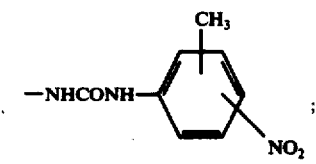

$R_5$ and $R_6$ are hydrogen and —$CH_3$; and A is hydrogen, alkali metal or alkaline earth, with the proviso that each A is identical in the same compound. Preferably, A is sodium or potassium.

Of particular interest are those compounds encompassed within general formula (I) which can be more specifically represented by general formula (II):

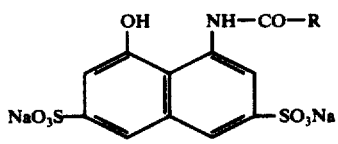
(II)

wherein R is selected from the group comprising

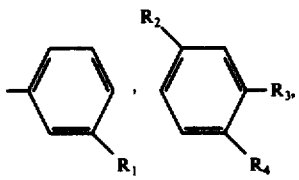

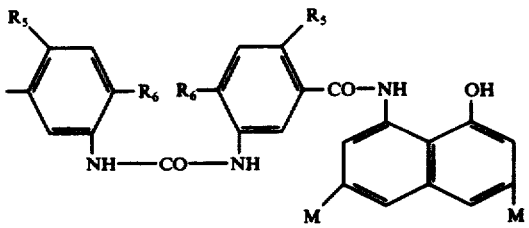

and

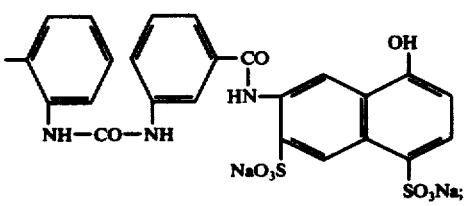

$R_1$ is

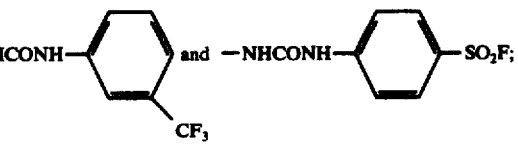

$R_2$ is hydrogen and —$CH_3$; $R_3$ is hydrogen, —$NO_2$, —$NH_2$ and —$CH_3$;
$R_4$ is hydrogen, —$NO_2$, —$NH_2$, —$CH_3$ and

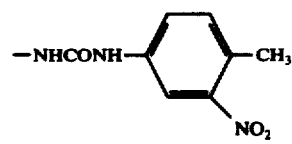

and $R_5$ and $R_6$ are hydrogen and —$CH_3$.

It has now been discovered that certain (substituted); 4-hydroxy-2,7-naphthalenedisulfonic acids and 4-hydroxy-2,7-naphthalenedisulfonic acid ureides interact with the complement reaction sequence, thereby inhibiting complement activity in body fluids.

This invention is particularly concerned with new compounds and their use which can be represented by formula (III)

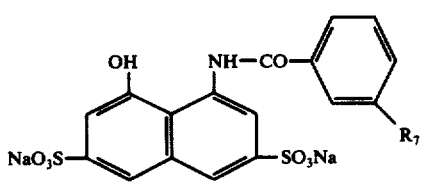

wherein R₇ is selected from the group comprising

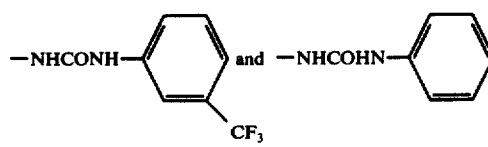

as well as with the use of known compounds which may be represented by formula (IV):

(IV)

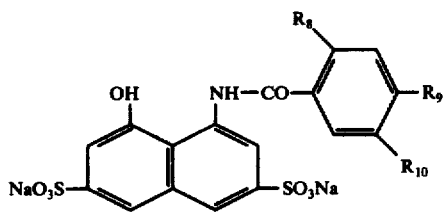

wherein $R_8$ = H and $CH_3$; $R_9$ = H; $NO_2$ and $CH_3$; $R_{10}$ = H; $NO_2$; $NH_2$; $CH_3$ and

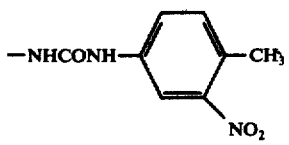

This invention is also concerned with the use of compounds of formula (V):

(V)

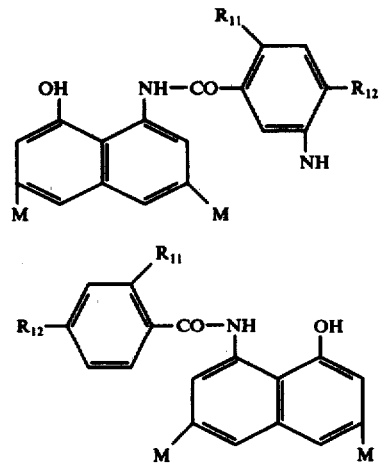

wherein $R_{11}$ = H and $CH_3$;
$R_{12}$ = and $CH_3$; and
M = $SO_3Na$; $SO_3H$ and with the use of the known compound of formula (VI):

(VI)

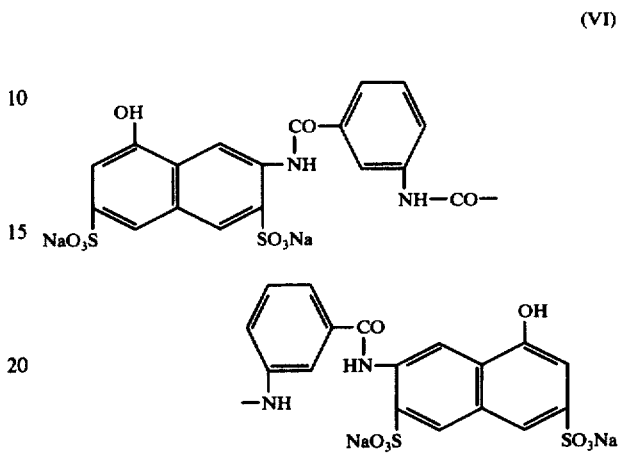

The following references disclose representative compounds of this invention: J. Chem. Soc., 3068 (1927); J. Chem. Soc., 3739 (1956); Biochem. J., 42, 109 (1948); Biochem. J., 47, 158 (1950); and Ann. Inst. Pasteur, 38, 81 (1924).

This invention is specifically concerned with the following new compounds and their use: 4-hydroxy-5-{m-[3-(α,α,α-trifluoro-m-tolyl)ureido]benzamido}-2,7-naphthalenedisulfonic acid, disodium salt; and 4-{m-{3-[p-(Fluorosulfonyl)phenyl]ureido}benzamido}-5-hydroxy-2,7-naphthalenedisulfonic acid, disodium salt. It is also concerned with the use of the following known compounds: 4-hydroxy-5-(p-nitrobenzamido)-2,7-naphthalenedisulfonic acid, disodium salt; 4-(p-Aminobenzamido)-5-hydroxy-2,7-naphthalenedisulfonic acid; disodium salt; 4-(4-Amino-m-toluamido)-5-hydroxy-2,7-naphthaleledisulfonic acid, disodium salt; 4-(4-Amino-m-toluamido)-5-hydroxy-2,7-naphthalenedisulonic acid, disodium salt; 4-hydroxy-5-(m-nitrobenzamido)-2,7-naphthalenedisulfonic acid, disodium salt; 4-(m-Aminobenzamido)-5-hydroxy-2,7-naphthalenedisulfonic acid, disodium salt; 4-hydroxy-5-{m-[3-(3-nitro-p-tolyl)ureido]benzamido}-2,7-naphthalenedisulfonic acid, disodium salt; 4-hydroxy-5-(5-nitro-o-toluamido)-2,7-naphthalenedisulfonic acid, disodium salt; 4-(5-Amino-o-toluamido)-5-hydroxy-2,7-naphthalenedisulfonic acid, disodium salt; 4-hydroxy-5-(3-nitro-p-toluamido)-2,7-naphthalenedisulfonic acid, disodium salt; 5,5'-[Ureylenebis(m-phenylenecarbonylimino)]bis-[4-hydroxy-2,7-naphthalenedisulfonic acid], tetrasodium salt; 4,4'-{Ureylenebis[(2-methyl-1,3-phenylene)-carbonyl]imino}bis[5-hydroxy-2,7-naphthalenedisulfonic acid]; and 3,3'-[Ureylenebis(m-phenylenecarbonylimino)]bis[5-hydroxy-2,7-naphthalenedisulfonic acid], tetrasodium salt.

The compounds of this invention may be prepared as shown by the examples herein and according to the methods described below. The compounds of the present invention may be prepared by acylation of the respective naphthylaminedisulfonic acid to the respective nitrobenzoyl derivative with a nitrobenzoyl chloride. The aminobenzoyl derivative is then formed by catalytic reduction of the nitro group, condensation with phosgene affords the respective s-carbamide; or condensation with the appropriate substituted phenylisocyanate affords unsymmetrical areas. Acidification produces the free acid. The following will illustrate the preparation of the compounds in more detail.

Schotten-Baumann acylation

To a solution of the sodium salt of a naphthylaminedisulfonic acid in an appropriate amount of water and 1N sodium hydroxide is added an appropriate nitrobenzoyl chloride. The mixture is shaken until no longer basic to test paper. Three additional equal portions of 1N sodium hydroxide are added, shaking between each addition until the solution is no longer basic. After the last portion of base is added, the reaction mixture is shaken for at least 30 minutes and then the still basic solution is acidified to Congo Red with concentrated hydrochloric acid. The reaction mixture is then copiously extracted with ether to remove the nitrobenzoic acid side product (by vacuum siphoning of the ethereal layer). The aqueous phase is then filtered to remove a small amount of the anhydride of the particular nitrobenzoic acid and the filtrate is concentrated in vacuo at 50°-60° C until a solid is precipitated. After cooling to ambient temperature, the product is filtered and is washed with saturated saline solution, 50% ethyl alcohol, absolute ethyl alcohol and ether.

Catalytic reduction

Treatment of a solution of the appropriate amount of the desired m-nitrobenzamide of naphthalenedisulfonic acid in 160-200 ml of water with 1.0-3.7 g of 10% palladium on carbon in a Parr apparatus under an initial hydrogen pressure of 42 pounds per square inch gives a theoretical uptake of hydrogen in 1¾ hours. The reaction mixture is filtered through diatomaceous earth and the catalyst is washed with water. The filtrate is concentrated under reduced pressure at 50°-60° to low volume and is then diluted with a large volume of absolute ethanol. The precipitated product is collected and is washed with absolute ethyl alcohol.

Phosgenation

Phosgene is bubbled through a mechanically stirred solution of the desired aminobenzamide of naphthalenedisulfonic acid in the appropriate amount of water containing a theoretical quantity of sodium carbonate until the reaction mixture becomes acidic to Congo Red. An additional quantity of carbonate is cautiously added and the process is repeated until the reaction mixture is again acidic. It is then neutralized with bicarbonate and is concentrated in vacuo at 50°-60° C. On cooling to room temperature a solid is formed which is filtered and is washed with 80% ethyl alcohol, absolute ethyl alcohol and ether.

Acylation with isocyanates

A solution of the appropriate amount of the desired m-aminobenzamide of naphthalenedisulfonic acid sodium salt in water is treated with a theoretical portion of the required isocyanate and is stirred vigorously for 6 hours at room temperature. The reaction mixture is diluted with additional water, is heated to approximatley 95° C to 30 minutes and is filtered through diatomaceous earth and is washed with hot water. The filtrate is treated with sodium chloride while heating on the steam bath and is allowed to stand at room temperature overnight (lower temperature is required in some cases). The precipitate is collected and is boiled with absolute ethyl alcohol then is allowed to stand at room temperature for several days. The product is then filtered and washed with absolute ethyl alcohol and ether.

This invention is concerned with a method of inhibiting the complement system in a body fluid, such as blood serum, which comprises subjecting body fluid complement to the action of an effective complement inhibiting amount of a compound encompassed within the formulae hereinabove. The method of use aspect of this invention is also concerned with a method of inhibiting the complement system in a warm-blooded animal which comprises internally administering to said animal an effective complement inhibiting amount of a compound encompassed within the formulae hereinabove. Body fluid can include blood, plasma, serum, synovial fluid, cerebrospinal fluid, or pathological accumulations of fluid as pleural effusion, etc.

Compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin, etc.) and inflammatory states induced by the action of bacterial or lysosomal enzymes on the appropriate complement components as for example, inflammation following coronary occlusion. They may also be useful in the treatment of transplant rejection and as blood culture or transport mediums.

DETAILED DESCRIPTION OF THE INVENTION

The following examples will serve to illustrate the invention in more detail.

EXAMPLE 1

4-Hydroxy-5-(4-nitro-3-toluamido)-2,7-naphthalenedisulfonic acid, disodium salt

A 76.5 g portion of 3-methyl-4-nitrobenzoic acid in 160 ml of thionyl chloride is refluxed for 2¾ hours (with complete solution occuring after 35 minutes). The solution is evaporated to an oil in vacuo and is reevaporated several times from toluene. The material is vacuum distilled at a bath temperature of 140°-150° C and at about 0.6 mm pressure. After rejecting the first few ml the fraction boiling at 107°-110° C is collected to give 81.1 g of 4-nitro-m-toluoyl chloride.

A 26.9 g portion of recrystallized 8-amino-1-naphthol-3,6-disulfonic acid monosodium salt is suspended in 125 ml of water along with 10.0 g of sodium acetate trihydrate, then 75 ml of 1N sodium hydroxide is added and 16.5 g of the product prepared above is added all at once, washing in with a small amount of diethyl ether. The mixture is shaken for 10 minutes and the addition of 1N sodium hydroxide with shaking is repeated twice, the final shake is continued for 45 minutes. The mixture is then acidified with 11 ml of concentrated hydrochloric acid and is extracted with six 150 ml portions of ether, the ether is removed each time by vacuum siphoning. The aqueous phase is neutralized with base and 6 drops of n-decyl alcohol is added to prevent frothing. The solution is concentrated in vacuo at about 55°–60° C until a solid begins to precipitate. The mixture is allowed to stand overnight at room temperature and is filtered. The precipitate collected is washed with 80% ethyl alcohol followed by absolute ethyl alcohol and ether. The product is dried overnight at 120° C then is dissolved in about 200 ml of boiling water and is diluted with 100 ml of absolute ethyl alcohol followed by 200 ml of 33⅓% ethyl alcohol. The thick mixture is triturated and allowed to stand overnight then is filtered and the product of the example is washed with 80% ethyl alcohol followed by absolute ethyl alcohol and ether.

EXAMPLE 2

4-(4-Amino-m-toluamido)-5-hydroxy-2,7-naphthalenedisulfonic acid, disodium salt A mixture of 25.0 g of 4-hydroxy-5-(4-nitro-3-toluamido)-2,7-naphthalenedisulfonic acid, disodium salt, 200 ml of distilled water and 2.5 g of 10% palladium on charcoal is hydrogenated in a Parr shaker for 3 hours at room temperature during which time 12 pounds of hydrogen is absorbed. The mixture is heated to dissolve some precipitated product and is filtered hot to remove the catalyst. The filtrate is then evaporated to a low volume in vacuo at 55°–60° C and is diluted with a large amount of absolute ethyl alcohol. The precipitate formed is triturated with a glass rod to break up any lumps and is allowed to stand at room temperature overnight then is filtered and is washed with absolute ethyl alcohol and ether. The product of the example is then oven dried at 120° C overnight.

EXAMPLE 3

4-Hydroxy-5-(m-nitrobenzamido)-2,7-naphthalenedisulfonic acid, disodium salt A 44.1 g portion of recrystallized 4-amino-5-hydroxy-2,7-naphthalenedisulfonic acid, mono sodium salt and 16.5 g of sodium acetate trihydrate is suspended in 40 ml of distilled water, then 120 ml of 1N sodium hydroxide is added and 44.55 g of m-nitrobenzoyl chloride is added all at once washing in with a small amount of diethyl ether. The resulting mixture is shaken for 5 minutes and another 120 ml of 1N sodium hydroxide is added and the mixture is shaken for ½ hour. The latter addition and shaking is repeated two more times. The resulting clear solution is acidified to Congo Red indicator paper with concentrated hydrochloric acid and is concentrated in vacuo at about 55° until a precipitate forms which is collected by filtration. The filtrate is set aside and the precipitate is ground up and is stirred with about 400 ml of ether for 20 minutes then is filtered and the precipitate is set aside. The filtrate previously set aside is extracted 3 times with ether which is removed by vacuum siphoning after each extraction. The aqueous solution is then kept at 5° C overnight with formation of a precipitate which is also collected. The precipitate set aside above is combined with the present precipitate and is dissolved in 400 ml of boiling water. A 100 ml portion of 95% ethyl alcohol is added and the solution is kept at 5° C overnight with precipitation of the product of the example which is collected by filtration.

EXAMPLE 4

4-hydroxy-5-(p-nitrobenzamido-2,7-naphthalenedisulfonic acid disodium salt

In a manner similar to that of Example 3, 4-hydroxy-5-(p-nitrobenzamido-2,7-naphthalenedisulfonic acid disodium salt can be prepared from p-nitrobenzoyl chloride.

EXAMPLE 5

4-(m-Aminobenzamido)-5-hydroxy-2,7-naphthalenedisulfonic acid, disodium salt A mixture of 15.89 g of 4-hydroxy-5-(m-nitrobenzmido)-2,7-naphthalenedisulfonic acid, disodium salt, 150 ml of distilled water and 1.0 g of 10% palladium on charcoal is hydrogenated in a Parr shaker for 2 hours at room temperature during which time 7.5 pounds of hydrogen is absorbed. The mixture is heated to dissolve some precipitated product and is filtered hot to remove the catalyst. The filtrate is then evaporated to a low volume in vacuo at 55°–60° C and is diluted with a large amount of absolute ethyl alcohol. The precipitate formed is triturated with a glass rod to break up any lumps and is allowed to stand at room temperature overnight, then is filtered and is washed with absolute ethyl alcohol and ether to give the product of the example.

EXAMPLE 6

4-(p-aminobenzamido)-5-hydroxy-2,7-naphthalenedisulfonic acid disodium salt

In a manner similar to that of Examples 3 and 5 4-(p-aminobenzamido)-5-hydroxy-2,7-naphthalenedisulfonic acid disodium salt can be prepared.

EXAMPLE 7

4-Hydroxy-5-m-[3-($\alpha,\alpha,\alpha$-trifluoro-m-tolyl)ureido]benzamido-2,7-naphthalenedisulfonic acid, disodium salt A mixture of 3.0 g of 4-(m-amino-benzamido)-5-hydroxy-2,7-naphthalenedisulfonic acid, disodium salt, 37.5 ml of distilled water and 3.0 ml of m-trifluoromethylphenylisocyanate is stirred for 6 hours, then is heated on a steam bath and is filtered through diatomaceous earth and the filter is washed with hot water. The volume of filtrate is adjusted to 60 ml and is salted with 10 g of sodium acetate then is allowed to stand at room temperature overnight. The precipitate formed is collected by filtration and is washed on the filter with a small amount of absolute ethyl alcohol and a large amount of diethyl ether. The material is then oven dried at 120° C for 2 hours and is then redissolved in 35–40 ml of hot water. This solution is kept at 5° C overnight. The resulting precipitate is collected by filtration and is dried as above to give the product of the example.

EXAMPLE 8

4-{m-{3-[p-(Fluorosulfonyl)phenyl]ureido}benzamido}-5-hydroxy-2,7-naphthalenedisulfonic acid, disodium salt A mixture of 18.0 g of sulfanilyl fluoride, 20.0 g of p-nitrophenyl chloroformate and 95 ml of benzene (dried by distillation) is refluxed and stirred for 5 hours (a precipitate appears at about 4 hours). The mixture is then cooled and filtered, the precipitate is washed with cold benzene and is recrystallized from methylene chloride to give 19.86 g of p-(fluorosulfonyl)carbanilic acid p-nitrophenyl ester.

A mixture of 4.0 g of 4-(m-amino-benzamido)-5-hydroxy-2,7-naphthalenedisulfonic acid, disodium salt in 40 ml of dimethylformamide (dried over 4A molecular sieve) and 16 g of 3A molecular sieve (Linde-type 1/16 inch) is stirred one hour at room temperature, then 3.12 g of p-(fluorosulfonyl)carbanilic acid p-nitrophenyl ester in 16 ml of dried dimethylformamide is added and stirring is continued for an additional 18 hours at room temperature. The resulting mixture is then filtered through diatomaceous earth and the filter is washed with dried dimethylformamide. The combined filtrate and washing is poured into about one liter of diethyl ether resulting in formation of a solid which is collected by filtration to give the product of the example.

EXAMPLE 9

4-Hydroxy-5-m-[3-(3-nitro-p-tolyl)ureido]benzamido-2,7-naphthalenedisulfonic acid, disodium salt A mixture of 3.0 g of 4-(m-amino-benzamido)-5-hydroxy-2,7-naphthalenedisulfonic acid, disodium salt in 37.5 ml of distilled water and 3.0 g of 3-nitro-4-methylphenyl isocyanate is stirred for 6 hours to give a gelatenous mass which is centrifuged. The clear liquid is decanted off and the residue is filtered using absolute ethyl alcohol to wash the material in the filter. The product of the example is oven dried at 120° C.

EXAMPLE 10

4Hydroxy-5-(5-nitro-o-toluamido)-2,7-naphthlenedisulfonic acid, disodium salt

A mixture of 74.5 g of 2-methyl-5-nitrobenzoic acid and 160 ml of thionyl chloride is refluxed for 4¼ hours (complete solution after 1½ hours). The mixture is evaporated in vacuo to an oil then is reevaporated several times with toluene, finally about 300 ml of hexane is added resulting in formation of needles after standing at room temperature overnight. The material is collected by filtration and is washed with hexane to give 5-nitro-o-toluoyl chloride.

A 26.9 g portion of recrystallized 4-amino-5-hydroxy-2,7-naphthalenedisulfonic acid, mono sodium salt and 10.0 g of sodium acetate trihydrate is suspended in 125 ml of distilled water, then 75 ml of 1N sodium hydroxide is added and 16.5 g of 5-nitro-o-toluoyl chloride (prepared above) is added all at once washing in with a small amount of diethyl ether. The resulting mixture is shaken for 5 minutes. The addition of two more 75 ml portions of 1N sodium hydroxide is required with shaking for 45 minutes after the last addition. The mixture is then acidified with 13 ml of concentrated hydrochloric acid and is extracted with six 150 ml portions of diethyl ether which is removed by vacuum siphoning after each extraction. The aqueous phase is then neutralized with base and 6 drops of n-decyl alcohol is added to prevent frothing. The solution is then concentrated to a low volume in vacuo and is diluted with a saturated saline solution to produce a precipitate. The precipitated product is filtered very slowly and is washed with absolute ethyl alcohol followed by ether. The lumpy material is oven dried at 120° C for several hours then is dissolved in about 600 ml of boiling water and is diluted with 150 ml of absolute alcohol. The precipitate formed after standing at room temperature overnight is collected by filtration and is washed with absolute ethyl alcohol followed by ether then is oven dried overnight at 120° C to give the product of the example.

EXAMPLE 11

4-(5-Amino-o-toluamido)-5-hydroxy-2,7-naphthalenedisulfonic acid, disodium salt

A mixture of 25.0 g of 4-hydroxy-5-(5-nitro-o-toluamido)-2,7-naphthalenedisulfonic acid, disodium salt, 200 ml of distilled water and 2.5 g of 10% palladium on charcoal is hydrogenated in a Parr shaker for 5 hours at room temperature during which time 12 pounds of hydrogen is absorbed. The mixture is heated on a steam bath and is filtered through diatomaceous earth to remove the catalyst. The filter is washed with hot water and the filtrate is then evaporated to about 100 ml in vacuo at 55°-60° C with formation of crystals after standing at room temperature overnight. The product of the example is collected by filtration and is washed with absolute ethyl alcohol followed by ether then is oven dried at 120° C.

EXAMPLE 12

4-Hydroxy-5-(3-nitro-p-toluamido)-2,7-naphthalenedisulfonic acid, disodium salt

A mixture of 75.3 of 4-methyl-3-nitrobenzoic acid and 150 ml of thionyl chloride is refluxed for 4¼ hours in a 120° C oil bath (complete solution is achieved after about 2¼ hours). The mixture is evaporated in vacuo to an oil then is reevaporated several times with toluene. The material is then distilled at a bath temperature of 150° C and about 0.6 mm. The fraction collected at 105°-110° C is 4-methyl-3-nitrobenzoylchloride.

A 26.9 g portion of recrystallized 4-amino-5-hydroxy-2,7-naphthalenedisulfonic acid, mono sodium salt and 10.0 g of sodium acetate trihydrate is suspended in 125 ml of distilled water, then 75 ml of 1N sodium hydroxide is added and 16.5 g of 4-methyl-3;1 -nitrobenzoyl chloride is added all at once washing in with a small amount of diethyl ether. The procedure from this point on is identical to that in Example 8 with the exception that 11 ml of concentrated hydrochloric acid is used to acidify the mixture.

EXAMPLE 13

4-(3-Amino-p-toluamido)-5-hydroxy-2,7-naphthalenedisulfonic acid, disodium salt

A mixture of 25.0 g of 4-hydroxy-5-(3-nitro-p-toluamido)-2,7-naphthalenedisulfonic acid, disodium salt, 200 ml of distilled water and 2.5 g of 10% palladium on charcoal is hydrogenated in a Parr shaker for 3¼ hours at room temperature during which time 12 pounds of hydrogen is absorbed. The mixture is heated on a steam bath and is filtered through diatomaceous earth to remove the catalyst. The filter is washed with hot water and the filtrate is then evaporated to a low volume in vacuo at 55°-60° C and diluted with a large amount of absolute ethyl alcohol. The precipitate formed is triturated with a glass rod to break up any lumps and is allowed to stand at room temperature overnight, then is filtered and is washed with absolute ethyl alcohol and ether. The product of the example is oven dried at 120° C overnight.

EXAMPLE 14

5,5'-[Ureylenebis(m-phenylenecarbonylimino)]bis[4-hydroxy-2,7-naphthalenedisulfonic acid] tetrasodium salt A mixture of 11.32 g of 4-hydroxy-5-m-nitrobenzamido-2,7-naphthalenedisulfonic acid, disodium salt, 150 ml of distilled water and 0.5 g of 10% palladium on charcoal is hydrogenated in a Parr shaker for 3 hours at room temperature during which time 13 pounds of hydrogen is absorbed. The mixture is heated on a steam bath and is filtered through diatomaceous earth to remove the catalyst. The filter is washed with hot water and the filtrate is cooled to room temperature then 1.83 g of concentrated hydrochloric acid is added and the precipitate formed is dissolved by boiling. The aqueous is concentrated to about 175 ml and 100 ml of absolute ethyl alcohol is added and the resultant mixture is allowed to come to room temperature overnight. The precipitate formed which is 4-m-amino-benzamido-5-hydroxy-2,7-naphthalenedisulfonic acid 2-sodium salt is collected by filtration.

To a stirred solution of 10 g of the above product prepared in the same manner as described above and 34.5 g of anhydrous sodium carbonate in 250 ml of water is bubbled in phosgene at ambient temperature. After 2 hours an additional 17 g of sodium carbonate is added and the phosgene addition is continued for another hour. The precipitate formed is collected then is mixed with water and is neutralized with base, then is heated and filtered. The material collected is dissolved in 300 ml of hot water then is concentrated to 200 ml in vacuo. The gelatinous precipitate is collected by slow filtration then is stirred with 95% ethyl alcohol. The resulting product is filtered and is washed with diethyl ether to give the product of the example.

EXAMPLE 15

3,3'-{Ureylenebis[(4-methyl-1,3-phenylene)carbonyl]}·bis[2,3-dihydro-2-oxo-naphth[1,8-de]-1,3-oxazine-5,8-disulfonic acid] tetrasodium salt To a stirred solution of 10.0 g of 4-(5-amino-o-toluamido)-5-hydroxy-2,7-naphthalenedisulfonic acid, disodium salt (prepared as described in Example 9) and 21.4 g of anhydrous sodium carbonate in 250 ml of water is bubbled in phosgene for one hour at room temperature. Then an additional 21.4 g of sodium carbonate is added and phosgenation is continued for one hour and 25 minutes. The resulting mixture is neutralized with 16.5 g of sodium carbonate and is filtered and the filtrate is set aside for use in Example 14. The precipitate is washed with a small amount of water then is oven dried at 120° C for several hours to give the product of the example.

EXAMPLE 16

4,4'-{Ureylenebis[(2-methyl-1,3-phenylene)carbonyl]imino}bis[5-hydroxy-2,7-naphthalenedisulfonic acid]

The aqueous phase filtrate set aside at the conclusion of Example 13 is concentrated in vacuo at about 50°-60° C and is filtered. The filtrate is evaporated to dryness and is triturated with about 250 ml of boiling methyl alcohol then is filtered. This filtrate is then evaporated in vacuo to afford a brown solid which is dissolved in 10 ml of distilled water, the solution is then warmed on a steam bath and is diluted with about 30 ml of absolute ethyl alcohol to give a black viscous material. The supernatent is decanted and absolute alcohol is added to the residue with scratching to afford a precipitate which is collected by filtration. This material is dissolved in 10 ml of distilled water, is boiled then is treated with activated charcoal and filtered through diatomaceous earth. The filtrate is diluted 2 fold with absolute ethyl alcohol and the upper phase is decanted from a dark oil. The decanted liquid is acidified with concentrated hydrochloric acid and is evaporated to dryness in vacuo. The residue is dissolved in 5 ml of dimethylformamide and is filtered to remove sodium chloride, then is washed with 5 ml of dimethylformamide. The combined filtrate and washing is diluted with a few ml of methyl alcohol and a large volume of diethyl ether to yield a dark brown oil. The supernatent is decanted and acetone is added to the residue with scratching until a solid forms which is collected by filtration and is washed with acetone. The product of the example is then oven dried at 105° C overnight.

EXAMPLE 17

3,3'-[Ureylenebis(m-phenylenecarbonylimino)]bis[5-hydroxy-2,7-naphthalenedisulfonic acid] tetrasodium salt A 41.0 g portion of recrystallized 3-amino-5-hydroxy-2,7-naphthalenedisulfonic acid and 16.5 g of sodium acetate trihydrate is dissolved in 250 ml of distilled water, then 44.55 g of m-nitrobenzoyl chloride is added all at once along with 120 ml of 1N sodium hydroxide and a small amount of diethyl ether. The resulting mixture is shaken for 5 minutes and another 120 ml of 1N sodium hydroxide is added and the mixture is shaken for ½ hour. The latter addition and shaking is repeated 2 more times. The resulting mixture is acidified to Congo Red indicator paper with concentrated hydrochloric acid and is allowed to stand at 5° C for 17 hours. The solution is filtered and the filtrate is allowed to stand until a precipitate forms. The precipitate is stirred with about 400 ml of diethyl ether and is collected to give 5-hydroxy-3-m-nitrobenzamido-2,7-naphthalenedisulfonic acid, disodium salt.

A mixture of 15.5 g of the preceding compound (prepared in a manner as described above), 170 ml of distilled water and 1.02 g of 10% palladium on charcoal is hydrogenated in a Parr shaker for 1½ hours at room temperature during which time 8.5 pounds of hydrogen is absorbed. The mixture is heated to dissolve some precipitated product and is filtered hot to remove the catalyst. The filtrate is then evaporated to a low volume and the precipitate formed is collected with the aid of 95% ethyl alcohol and is washed with diethyl ether to give 3-(m-aminobenzamido)-5-hydroxy-2,7-naphthalenedisulfonic acid, disodium salt. To a stirred solution of 10 g of the above product prepared in the manner described above and 34.5 g of anhydrous sodium carbonate in 250 ml of water is bubbled in phosgene at ambient temperature. After one hour and 15 minutes an additional 34.5 g of sodium carbonate is added and the phosgene addition is continued until it is acidic again (5 hours). The solution is then neutralized with base and is filtered. The filtrate is concentrated and filtered and the final filtrate is concentrated and filtered. All the residues are combined and dissolved in 250 ml of hot water which is concentrated to 150 ml, is cooled and the precipitate formed is collected by filtration. The precipitate is dissolved in hot water and is concentrated to a low volume until a precipitate is formed which is collected by filtration with the aid of 95% ethyl alcohol to give the product of the example.

Example 18

| Preparation of Compressed Tablet | |
|---|---|
| Ingredient | mg/Tablet |
| Active Compound | 0.5–500 |
| Dibasic Calcium Phosphate NF | qs |
| Starch USP | 40 |
| Modified Starch | 10 |
| Magnesium Stearate USP | 1–5 |

Example 19

| Preparation of Compressed Tablet-Sustained Action | |
|---|---|
| Ingredient | mg/Tablet |
| Active Compound as Aluminum Lake*, Micronized | 0.5–500(as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

Example 20

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

Example 21

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

Example 22

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

Example 23

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

Example 24

| Preparation of Injectable Solution | |
|---|---|
| Ingredient | % W/V |
| Active Compound | 0.05–5 |
| Benzyl Alcohol NF | 0.9 |
| Water for Injection | 100.0 |

Example 25

| Preparation of Injectable Oil | |
|---|---|
| Ingredient | % |
| Active Compound | 0.05–5 |
| Benzyl Alcohol | 1.5 |
| Sesame Oil qs ad | 100.0 |

Example 26

| Preparation of Intra-Articular Product | |
|---|---|
| Ingredient | Amount |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs to | 100% |

Example 27

| Preparation of Injectable Depo suspension | |
|---|---|
| Ingredient | % W/V |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

The compounds of this invention may be administered internally, e.g., orally, or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers.

The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of representative compounds of this invention has been demonstrated by one or more of the following identified tests: (i) Test, Code 026 (C1 inhibitor). This test measures the ability of activated human fluid phase human C2 in the presence of C4 and appropriate dilutions of the test compound. An active inhibitor protects C2 from C1 and C4; (ii) Test, Code 035 (C3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forsssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed quinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

Table I shows that representative compounds of the invention possess complement inhibitory activity.

TABLE I

Biological Activities

| | Assay Results | | | | |
|---|---|---|---|---|---|
| | In Vitro | | | In Vivo | |
| Compound | 026* | 035 | 036 | Forsssman | % Reduction Complement |
| 4-Hydroxy-5-{m-[3-(α,α,α-trifluoro-m-tolyl)-ureido]benzamido}-2,7-naphthalenedisulfonic acid, disodium salt | 1** | NEG | NEG | 5 | −6 |
| 4-{m-{3-[p-(Fluorosulfonyl)phenyl]ureido}-benzamido}-5-hydroxy-2,7-naphthalenedisulfonic acid, disodium salt | 4 | NEG | NEG | — | — |
| 4-Hydroxy-5-(4-nitro-3-toluamido)-2,7-naphthalenedisulfonic acid, disodium salt | 2 | NEG | NEG | 48 | −20 |
| 4-(4-Amino-m-toluamido)-5-hydroxy-2,7-naphthalenedisulfonic acid, disodium salt | 5 | NEG | NEG | 17 | +12 |
| 4-Hydroxy-5-{m-[3-(3-nitro-p-tolyl)ureido]-benzamido}-2,7-naphthalenedisulfonic acid, disodium salt | NEG | NEG | NEG | 15 | +46 |
| 4-Hydroxy-5-(5-nitro-o-toluamido)-2,7-naphthalenedisulfonic acid, disodium salt | 2 | NEG | NEG | 10 | −17 |
| 4-(5-Amino-o-toluamido)-5-hydroxy-2,7-naphthalenedisulfonic acid, disodium salt | 2 | NEG | NEG | — | — |
| 4-Hydroxy-5-(3-nitro-p-toluamido)-2,7-naphthalenedisulfonic acid, disodium salt | 3 | NEG | NEG | — | — |
| 4-(3-Amino-p-toluamido)-5-hydroxy-2,7-naphthalenedisulfonic acid, disodium salt | 5 | NEG | NEG | — | — |
| 5,5′-[Ureylenebis(m-phenylenecarbonylimino)]-bis[4-hydroxy-2,7-naphthalenedisulfonic acid] tetrasodium salt | 6 | 1 | 2 | — | — |

TABLE I-continued

| | Biological Activities | | | | |
| --- | --- | --- | --- | --- | --- |
| | Assay Results | | | | |
| | In Vitro | | | In Vivo | |
| Compound | 026* | 035 | 036 | Forssman | % Reduction Complement |
| 4,4'-{Ureylenebis[(2-methyl-1,3-phenylene)-carbonyl]imino}bis[5-hydroxy-2,7-naphthalene-disulfonic acid] | 7 | 3 | 3 | — | — |
| 3,3'-[Ureylenebis(m-phenylenecarbonylimino)]-bis[5-hydroxy-2,7-naphthalenedisulfonic acid], tetrasodium salt | 5 | 2 | 2 | 35 | −31 |

*Tests identified by code herein.
**Numbers represent activity in wells. a serial dilution assay, higher well number indicates higher activity. The serial dilutions are two-fold.

We claim:

1. A compound selected from those of the formula:

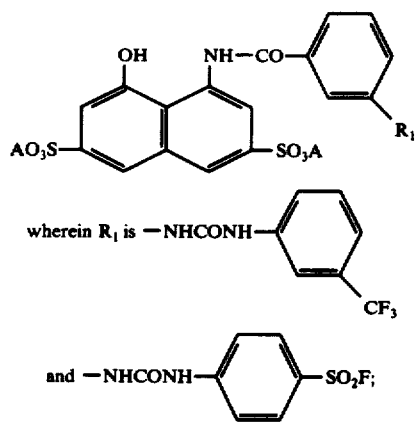

wherein $R_1$ is —NHCONH—⌬—CF$_3$ and —NHCONH—⌬—SO$_2$F;

and A is hydrogen, alkali metal or alkaline earth metal, with the proviso that each A is identical in the same compound.

2. A compound selected from those of the formula:

wherein $R_7$ is

—NHCONH—⌬—CF$_3$ ; and —NHCONH—⌬—SO$_2$F.

3. A compound according to claim 2, 4-hydroxy-5-{m-[3-(α,α,α-trifluoro-m-tolyl)ureido]benzamido}-2,7-naphthalenedisulfonic acid, disodium salt.

4. A compound according to claim 2, 4-{m-{3-[p(fluorosulfonyl)phenyl]ureido}benzamido}-5-hydroxy-2,7-naphthalenedisulfonic acid, disodium salt.

* * * * *